United States Patent [19]

Blaney et al.

[11] Patent Number: 5,399,177
[45] Date of Patent: Mar. 21, 1995

[54] REFASTENABLE ADHESIVE FASTENING SYSTEMS FOR DISPOSABLE ABSORBENT ARTICLES

[75] Inventors: Ted L. Blaney, West Chester; M. Elizabeth P. Chisholm, Cincinnati, both of Ohio

[73] Assignee: The Procter & Gamble Company, Cincinnati, Ohio

[21] Appl. No.: 782,707

[22] Filed: Oct. 25, 1991

[51] Int. Cl.⁶ ............................................. A61F 13/15
[52] U.S. Cl. ...................................... 604/389; 604/390
[58] Field of Search ........................ 604/389–391, 604/385.1

[56] References Cited

U.S. PATENT DOCUMENTS

| | | | |
|---|---|---|---|
| 3,089,494 | 5/1963 | Schwartz | 604/389 |
| 3,630,201 | 12/1971 | Endres . | |
| 3,646,937 | 3/1972 | Gellert . | |
| 3,848,594 | 11/1974 | Buell . | |
| 3,853,129 | 12/1974 | Kozak . | |
| 3,867,940 | 2/1975 | Mesek et al. | 604/390 |
| 3,921,638 | 11/1975 | Schaar | 604/390 |
| 3,971,380 | 7/1976 | Tritsch . | |
| 4,010,753 | 3/1977 | Tritsch . | |
| 4,182,333 | 1/1980 | Schaar | 604/390 |
| 4,237,889 | 12/1980 | Gobran . | |
| 4,376,147 | 3/1983 | Byrne et al. . | |
| 4,436,520 | 3/1984 | Lipko et al. . | |
| 4,540,415 | 9/1985 | Korpman . | |
| 4,655,761 | 4/1987 | Grube et al. | 604/389 |
| 4,710,190 | 12/1987 | Wood et al. . | |
| 4,728,325 | 3/1988 | Spiller . | |
| 4,743,242 | 5/1988 | Grube et al. . | |
| 4,753,649 | 6/1988 | Pazdernik | 604/389 |
| 4,762,888 | 8/1988 | Sun et al. . | |
| 4,769,283 | 9/1988 | Sipinen et al. . | |
| 4,880,422 | 11/1989 | McBride . | |
| 4,894,060 | 1/1990 | Nestegard | 604/391 |
| 4,973,326 | 11/1990 | Wood et al. | 604/391 |
| 4,983,174 | 1/1991 | Noreen et al. . | |
| 5,019,071 | 5/1991 | Bany et al. . | |
| 5,019,072 | 5/1991 | Polski . | |
| 5,024,672 | 6/1991 | Widlund | 604/390 |
| 5,026,446 | 6/1991 | Johnston et al. . | |
| 5,061,262 | 10/1991 | Chen et al. | 604/389 |
| 5,066,289 | 11/1991 | Polski | 604/389 |
| 5,106,383 | 4/1992 | Mulder et al. | 604/389 |
| 5,147,347 | 9/1992 | Huang et al. | 604/390 |

FOREIGN PATENT DOCUMENTS

| | | |
|---|---|---|
| 0316601A2 | 5/1989 | European Pat. Off. . |
| 0336639A2 | 10/1989 | European Pat. Off. . |
| 0418951A2 | 3/1991 | European Pat. Off. . |
| 1597799 | 9/1981 | United Kingdom . |
| WO88/07336 | 10/1988 | WIPO . |

Primary Examiner—Randall L. Green
Assistant Examiner—K. M. Reichle
Attorney, Agent, or Firm—Steven W. Miller; E. Kelly Linman; Jacobus C. Rasser

[57] ABSTRACT

Disposable absorbent articles such as baby diapers or adult incontinent briefs provided with a refastenable adhesive fastening system. The adhesive fastening system preferably comprises a pair of tape tabs each having an adhesive surface which during use is adhered to a landing member having an adherence surface which may comprise only the backsheet that has no reinforcement for strength against tearing or may comprise a reinforced backsheet. The invention improves bond security while at the same time making the fastening system more easy to remove without tearing by careful optimization of the properties of the adhesive, the tape tab, and the landing member. In particular, it has been found that the adhesive fastening system should have a Standard Shear Hang Time of greater than about 1000 minutes per square inch. The surface characteristics, toughness, and elasticity modulus of the landing member is optimized while the adhesive aggressiveness (quick-stick) of the adhesive is optimized with preferred low coating weights of the adhesive and low calculated caliper for the landing member so as to provide an adhesive fastening system that bonds easily, holds securely and is refastenable.

12 Claims, 1 Drawing Sheet

REFASTENABLE ADHESIVE FASTENING SYSTEMS FOR DISPOSABLE ABSORBENT ARTICLES

FIELD OF THE INVENTION

The present invention relates to adhesive fastening systems for disposable absorbent articles like baby diapers or adult incontinent briefs, and, more particularly, to a refastenable adhesive fastening system that bonds easily, holds securely, and is easily reopened and refastened without tearing the landing member even if the landing member consists of a low caliper polyethylene film backsheet having no reinforcement for strength against tearing.

BACKGROUND OF THE INVENTION

Disposable absorbent articles like baby diapers or adult incontinent briefs are well-known in the art and commercially sold on a broad scale. Many of the commercially available diapers or briefs comprise an adhesive tape fastening system to secure the articles on a baby or an incontinent adult. The performance of the fastening system represents a key element for the functionality of such articles and therefore contributes to the commercial success of absorbent articles incorporating adhesive tape fastening systems.

This fact is reflected in the vast amount of references concerned with disposable absorbent articles having adhesive fastening systems. In particular, adhesive fastening systems which allow the absorbent article to be opened and reclosed in order to check whether a change is indicated, often referred to as "refastenable" systems, have found much attention in the art.

The design of adhesive fastening systems for disposable absorbent articles concentrates on two major criteria which are generally opposed to each other: adhesive bond security and refastenability. It is the goal of such adhesive fastening systems to achieve both strong adhesive bond security (a bond which remains adhered during use) and non-destructive removal of the tapes for refastenability. It has generally been believed that the peel force of a pressure-sensitive adhesive tape from a substrate is one of the most important factors in determining how an adhesive fastening system actually performs during use. The peel force property shows that higher peel forces improve the bond security of the fastening system while also making it more difficult to remove without tearing the landing member. Thus, early solutions to providing an improved adhesive fastening system focused on balancing the peel force in order to optimize bond security and refastenability. One focus area was on adjusting the properties of the elements of the adhesive fastening system. Particularly, the tensile strength (tear resistance) of the landing member, typically the unreinforced backsheet of the absorbent article, was increased so that the backsheet could withstand high tensile stresses caused by the tape removal. However, such backsheets tended to be rigid, noisy, expensive and more burdensome on material resources and the environment (require more materials). Conversely, the tape properties were adjusted to increase contact area and lower peel force so as to not exceed the strength of the backsheet. These systems were expensive, inconvenient and had low bond security at low application pressure. As the demand was made for high bond security adhesive fastening systems to meet the in-use conditions placed upon absorbent articles, additional strength had to be added to the backsheet to avoid its tearing. This additional strength was added to the backsheet by increasing its thickness, and/or by reinforcing it such as by laminating additional materials to the inside or outside of the backsheet in the fastening area.

For example, U.S. Pat. Nos. 3,875,621 and 3,931,666 each disclose adhesive tapes for diapers that provide refastenability by transferring a target tape to the backsheet thus preventing destruction of the backsheet when detaching the tape and providing a target surface for refastening it. In U.S. Pat. Nos. 3,950,824, 4,067,337, and 4,769,283 refastenability is approached by providing particular adhesive surfaces, selecting particular adhesive materials, subdividing the adhesive surface into small areas or using different adhesive materials on different portions of the adhesive tape surface. These approaches to refastenability resulted in additional cost and complexity when manufacturing the articles and some also made usage of the articles by consumers more complex.

U.S. Pat. Nos. 4,237,889, 4,389,212 and 4,769,283 disclose improved tape backing materials and tape backing designs. These improvements attempt to reduce tape backing failure by providing cross-directional elasticity or improved flexibility and softness of the tape backing material.

U.S. Pat. Nos. 3,867,940, 4,296,750 and 4,983,174 are directed towards reinforcing the backsheet in order to prevent tearing of the backsheet upon opening of the adhesive fastening system. In particular, a coating of a hot melt adhesive on the backsheet as well as application of an additional layer of film material to reinforce the backsheet were disclosed and have found wide use, especially on baby diapers. This solution provides simplified refastenable adhesive tape fastening systems for the user over the target tape type of fastening systems since a single piece refastenable tape of high adhesive strength can be used without destroying the backsheet material. However, these systems increase the manufacturing complexity, the cost of the article and the environmental burden upon disposal of articles containing the extra reinforcement materials.

U.S. Pat. Nos. 4,655,761, 4,743,242 and 4,880,422 appear to address part of the above problems with reinforcing systems by providing backsheets capable of accepting adhesive tapes without reinforcement areas. These references focus on strengthening the backsheet material by selecting particular polymer film material compositions or embossing patterns. However, in order to maintain the prime function of the adhesive tape, namely to securely adhere to the backsheet of the disposable article, these systems require high tape peel force values, thereby compromising refastenability of the tape with the enhanced probability of destroying the backsheet. Further, the problem of bond security is aggravated by "deep embossing" (i.e., more than 50 microns) of the backsheet which reduces the available adhesive contact area.

U.S. Pat. Nos. 4,540,415 and 4,728,325 disclose special adhesive compositions or polymer film compositions for backsheets to provide refastenability. However, their technical, economical and/or ecological performance have heretofore not resulted in commercial availability of low cost refastenable adhesive tape fastening systems.

In general, all adhesive fastening systems for disposable absorbent articles have sought to balance the competing technical demands of refastenability, contamination sensitivity, initial adherence and long term bond strength with economical, ecological and convenience requirements. However, none of the commercially available adhesive fastening systems is currently able to meet all demands and requirements. The essential technical performance of adhesive tape fastening systems has been provided by systems employing aggressive adhesive tapes on backsheets with expensive reinforcement areas or multi-layer adhesive tape systems with transferable target tapes which have low consumer acceptance due to their complexity. These systems are especially unsuitable for incontinent briefs where the cost of such complex systems are much greater since the briefs are much larger and the range of the physical dimensions of the wearer is greater requiring larger area landing members to provide adjustability. Further, recent environmental concerns have dictated the use of less material. However, simple, low cost and low material consumption adhesive fastening systems are not available without compromising bond security or refastenability.

Therefore, an object of the present invention is to provide an adhesive fastening system having the essential technical bond security and fastening performance while providing refastenability without tearing of the landing member.

A further object of the present invention is to reduce or maintain the amount of materials used in the construction of the adhesive fastening system thereby providing ecologically and economically acceptable disposable absorbent articles.

A still further object of the present invention is to provide superior bond security and superior refastenability when the landing member is a reinforced backsheet.

An additional object of the present invention is to provide disposable absorbent articles with a low cost, refastenable, adhesive fastening system by using only the low caliper backsheet as the landing member.

Yet another object of the present invention is to provide a disposable incontinent brief or baby diaper using the refastenable adhesive tape fastening systems according to the present invention.

These and other objects of the present invention will be more readily apparent when considered in reference to the following description and when taken in connection with the accompanying drawings.

SUMMARY OF THE INVENTION

According to the present invention, a disposable absorbent article such as a baby diaper or an adult incontinent brief is provided with a refastenable adhesive fastening system. The fastening system preferably comprises a pair of tape tabs each having an adhesive surface which during use is adhered to a landing member having an adherence surface which may comprise only the backsheet of the disposable absorbent article that has no reinforcement for strength against tearing or may comprise a reinforced backsheet. In particular, the present invention provides an adhesive tape fastening system that bonds easily, holds securely, and is refastenable (i.e., delaminating and readhering of the adhesive of the tape tab to the backsheet without damaging the backsheet).

The present invention improves the bond security while at the same time making it more easy to remove from a low caliper polyethylene backsheet without tearing by careful optimization of the properties of the adhesive tape and the landing member (backsheet). These properties are optimized and measured using evaluation techniques and methods which are much more predictive of the key consumer performance attributes of such adhesive fastening systems. In particular, by matching the physical properties of the tapes, their backing materials, and the landing member (backsheet), the adhesive fastening system can give the desired refastenability without extra reinforcing materials or parts and without sacrificing bond security.

A test of how an adhesive bond behaves when it is under wearing tension on a diaper and that best simulates a wide range of design, environmental and consumer variables is a shear hang test. The shear hang test measures how long an adhesive bond can hold against a given tension in the shear mode. Results of a modified shear hang test at typical conditions show a very good correlation with consumer use performance. Thus, it has been found that the adhesive fastening system should have a Standard Shear Hang Time of greater than about 1000 minutes per square inch, log (SHT) of 3.0, under standard test conditions, and a Modified Shear Hang Time of greater than about 500 minutes per square inch, log (MSHT) of 2.7, under modified test conditions as hereinafter described.

In another aspect of the present invention, the bond security and refastenability can be enhanced by providing a landing member that has certain defined surface characteristics. The adherence surface of the landing member is textured such that it has a surface roughness having a Mean Leveling Depth of between about 2 microns and about 20 microns. These surface characteristics enhance the bond security of the adhesive fastening system.

There are two mechanisms of tape failure that have some variables in common and several important variable differences. The two mechanisms of failure are: creep, which is the very slow flow of the adhesive under stress that causes the adhesive to pull free from the adherence surface of the landing member; and crack propagation, which results when the build up of stress initiates a crack which proceeds rapidly along the adhesive/landing member interface until the stress energy is spent. The shear hang tests report the failure by either mechanism. Rough substrate surfaces and soft (amorphous, flowable) adhesives tend to promote creep failure while smooth substrate surfaces and hard (crystalline) adhesives tend to promote crack propagation failures. Either mechanism contributes to failure during use of adhesive fastening systems on disposable absorbent articles and are best avoided by balancing the properties of the adhesive and substrate that contribute to these failure mechanisms.

Thus, in another aspect of the present invention, the properties of the tape (adhesive) and the landing member are matched to minimize these failure mechanisms.

When the fastening system is subjected to stress conditions due to the wearer's movements during use, the tape and the landing member stretch under load. If there is too large a difference in their elongation properties, then stress is transferred to the adhesive bond which may cause peel forces which cause premature failure of the adhesive bond. If the tape and the landing member have similar elongation or stretch properties, then the stress transferred to the adhesive bond is minimized and the bond tends to remain in a shear mode of failure which is stronger. Thus, in the present invention, it has been found that the Youngs Modulus (elasticity modulus) of the landing member should be increased to more closely match the elasticity modulus of the tape (within a factor of at least about 2 or 3). Therefore, the landing member, the backsheet, preferably has a Youngs Modulus (elasticity modulus) of greater than about 175 N/mm$^2$ in order to withstand higher stress at greater elongation.

The adhesive aggressiveness (quick-stick) to the landing member determines the bonding strength of the fastening system at light application pressures. This aggressiveness needs to be controlled so as to maximize the strength of the bond but also so as to minimize the energy transmitted to the landing member when the tapes are removed (especially when the tapes are "jerked" off). The toughness, impact resistance or impact energy, of the landing member provides a measure of the maximum rate that this force can be transferred without initiating a crack or tear type failure of the landing member. Thus, the adhesive is preferred to have a quick-stick of at least about 150 g/cm while the landing member, the backsheet, has a toughness as measured by an impact test of greater than about 1200 ergs.

The improved bond security and refastenability of the adhesive fastening system can be achieved without the need for reinforcing the landing member (which reduces the cost and improves the environmental impact of the adhesive fastening system) and with a minimum of materials (which reduce cost and improve ease of use and aesthetics.) The coating weight of the adhesive can be relatively low, preferably less than about 22 g/m$^2$. Further, the backsheet, which does not need to be reinforced, can have a relatively low calculated caliper (nominal average thickness) of between about 0.02 mm (0.8 rail) and about 0.036 mm (1.4 mils).

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawing in which like designations are used to designate substantially identical elements, and in which:

DETAILED DESCRIPTION OF THE INVENTION

Figure 1:
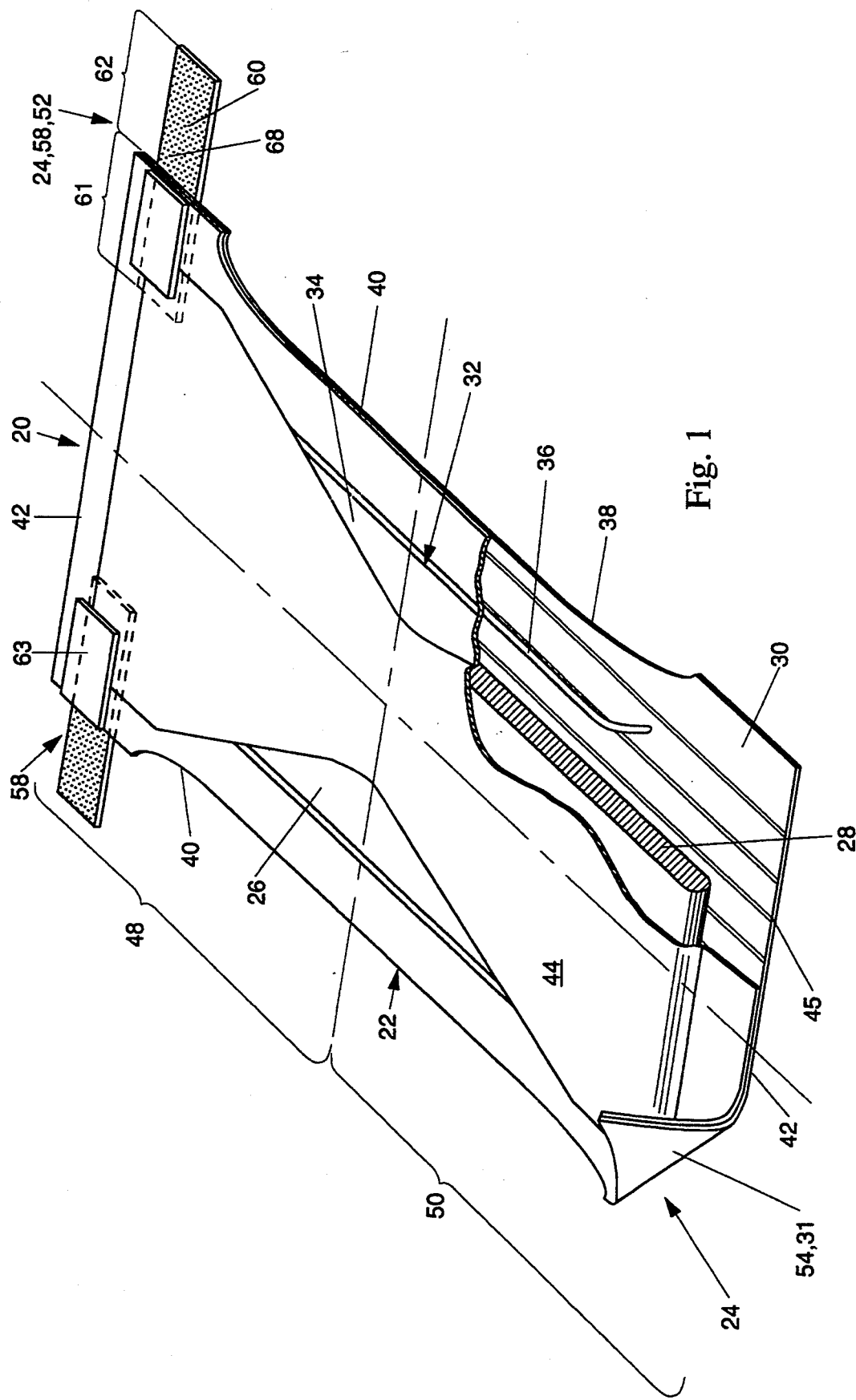
FIG. 1 is a partially cut-away perspective view of a disposable absorbent article (incontinent brief) incorporating the refastenable adhesive tape fastening system of the present invention.

Refastenable adhesive fastening systems of the present invention are useful and beneficial when applied to disposable absorbent articles. As used herein, the term "disposable absorbent article" refers to articles which absorb and contain body exudates and more specifically refers to articles which are placed against or in proximity to the body of the wearer to absorb and contain the various exudates discharged from the body of the wearer and which are not intended to be laundered or otherwise restored or reused as an absorbent article (i.e., they are intended to be discarded after a single use and, preferably, to be recycled, composted or otherwise disposed of in an environmentally compatible manner).

A preferred embodiment of a disposable absorbent article of the present invention is an adult incontinent brief or diaper, shown in FIG. 1 as diaper 20. As used hereinafter, the term "diaper" refers to an absorbent article generally worn by infants and incontinent persons that is drawn up between the legs and fastened about the waist of the wearer. Examples of the kind of diapers to which the present invention is readily adapted are shown in U.S. Pat. Nos. Re. 26,151; B2 3,860,003; 4,253,461; and 4,704,115. Each of these patents are incorporated herein by reference. It will be apparent from the following description that the refastenable adhesive fastening system illustrated and described herein may be applied to the body portion of such diapers. On the other hand, it will be understood that the invention is not limited to any specific diaper structure or configuration, provided it has a fastening system and is compatible with the requirements of the disposable absorbent articles disclosed herein.

Referring to the drawing, it will be noted that FIG. 1 is a partially cut-away perspective view of the diaper 20 according to the present invention prior to its being placed on a wearer. As can be seen in FIG. 1, a preferred diaper 20 comprises a body portion 22 and a refastenable adhesive tape fastening system designated generally as 24. A preferred body portion 22 comprises a liquid previous topsheet 26, an absorbent core 28, a liquid impervious backsheet 30, and elastically contractible leg cuffs 32 comprising a side flap 34 and one or more elastic members 36. (For simplicity purposes, only one elastic member is shown in the drawings although more than one strand can be positioned in each side flap 34.) While the topsheet 26, the absorbent core 28, the backsheet 30, the side flaps 34, and the elastic members 36 may be assembled in a variety of well known configurations, a preferred diaper configuration is shown and described generally in the above-referenced U.S. Pat. No. B2 3,860,003 which issued to Kenneth B. Buell on Jan. 14, 1975 and in U.S. Pat. No. 4,253,461 which issued to Strickland & Visscher on Mar. 3, 1981.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extent of the body portion 22. The periphery 38 comprises the longitudinal edges 40 and the end edges 42.

The body portion 22 has an inside surface 44 and an outside surface 45. In general, the outside surface 45 of the diaper 20 extends from one end edge 42 to the other end edge 42 of the diaper and from one longitudinal edge 40 to the other longitudinal edge 40 of the diaper and is the surface farthest from the wearer during use of the diaper 20. The backsheet 30 preferably forms most of the outside surface 45 of the body portion 22. The inside surface 44 is that surface of the diaper opposite the outside surface 45 and in the embodiment shown is preferably formed by the topsheet 26. Preferably, the inside surface 44 of the diaper 20 is coextensive with the outside surface 45 and in general the inside surface 44 is for the greater part in contact with the wearer when the diaper 20 is worn.

The diaper 20 has first and second end regions 48 and 50, respectively, extending from the end edges 42 of the diaper periphery 38 toward the lateral centerline of the diaper 20. Both the first end region 48 and the second end region 50 extend a distance of about one-half of the length of the diaper 20 such that the end regions comprise each half of the diaper 20.

The absorbent core 28 of the body portion 22 may be any absorbent means which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, asymmetric, T-shaped, etc.) and from a wide variety of liquid absorbent materials commonly used in diapers and other disposable absorbent articles such as comminuted wood pulp which is generally referred to as airfelt. Examples of other suitable absorbent materials include creped cellulose wadding, meltblown polymers including conform, cross-linked cellulosic fibers, tissue including tissue wraps and tissue laminates, absorbent foams, absorbent sponges, superabsorbent polymers, absorbent gelling materials, or any equivalent materials or combination of materials. The configuration and construction of the absorbent core may also be varied (e.g., the absorbent core may have varying caliper zones, a hydrophillic gradient, a superabsorbent gradient, or lower average density and lower average basis weight acquisition zones; or may comprise one or more layers or structures). The total absorbent capacity of the absorbent core 28 should, however, be compatible with the design exudate loading and the intended use of the diaper 20. Further, the size and absorbent capacity of the absorbent core 28 may be varied to accommodate wearers ranging from infants to adults.

A preferred embodiment of the diaper 20 has an hourglass-shaped absorbent core 28. An exemplary absorbent structure for use as the absorbent core is described in U.S. Pat. No. 4,610,678, entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton and Gellert on Jun. 16, 1987; and U.S. Pat. No. 4,888,231 entitled "Absorbent Core Having A Dusting Layer" issued to Angstadt on Dec. 19, 1989; also describe absorbent structures that are useful in the present invention. The absorbent core 28 is preferably the commercially successful absorbent member described in U.S. Pat. No. 4,834,735, entitled "High Density Absorbent Members Having Lower Density and Lower Basis Weight Acquisition Zones" issued to Alemany and Berg on May 30, 1989. Other preferred absorbent cores are described in U.S. Pat. Nos. 4,685,915 and 4,781,710 as comprising fibrous structures having areas of different absorbent capacity, density, or liquid acquisition speed. An alternative thin absorbent core useful in the present invention may be found in U.S. Pat. No. 4,600,458. Each of these patents are incorporated herein by reference.

The absorbent core 28 is superposed on the backsheet 30 and is preferably joined thereto by a core attachment means (not shown) such as those well known in the art, for example, pressure-sensitive adhesives, hot melt adhesives or other adhesives; ultrasonic bonds; heat/pressure bonds; dynamic mechanical bonds; or any other suitable attachment means or combinations of these attachment means as are known in the art. For example, the absorbent core 28 may be secured to the backsheet 30 by a uniform continuous layer of adhesive, a patterned layer of adhesive, or a network of adhesive filaments such as any array of separate lines, spirals, or spots of adhesive. Adhesives which have been found to be satisfactory are preferably hot melt adhesives such as manufactured by Century Adhesives, Inc., of Columbus, Ohio and marketed under the tradename Century 5227; and by H. B. Fuller Company of St. Paul, Minn. and marketed as HL-1258. The core attachment means preferably comprise an open pattern network of filaments of adhesive as is shown in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference.

The backsheet 30 is impervious to liquids (e.g., urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet 30 prevents the exudates absorbed and contained in the absorbent core 28 from soiling articles which contact the diaper 20 such as bedsheets and undergarments. The backsheet may thus comprise polymeric films such as thermoplastic films of polyethylene or polypropylene, or composite materials such as a film-coated nonwoven material. For economic, aesthetic, and ecological reasons, the backsheet 30 preferably has an average nominal caliper, calculated caliper, of less than about 0.036 mm (1.4 mils), more preferably a calculated caliper of from about 0.020 mm (0.8 mil) to about 0.036 mm (1.4 mils), most preferably from about 0.025 mm (1.0 mil) to about 0.030 mm (1.2 mil).

Preferably, the backsheet 30 is a flexible polyethylene film. As used herein the term "polyethylene" film refers to films which are essentially made of polyethylene, however, it is understood that polyethylene film will contain a variety of additives to provide characteristics like opacity, strength requirements, color, or any other desired characteristic that can be achieved through adding minor amounts of other substances than polyethylene into the films. The total amount of additives should be less than 45%, preferably less than 15%, by weight of film materials. Particularly for opacity of the film, titanium dioxide is commonly used in a range of 2-6%, preferably 3.5-4.8%, by weight of the film. Exemplary films for use as the backsheet of the present invention are manufactured by Tredegar Industries, Inc. of Terre Haute, Ind. under the designation X-8526. The backsheet 30 is preferably textured as described hereinafter to enhance the performance of the fastening system and to provide a more clothlike appearance. Further, the backsheet 30 may also permit vapors to escape from the absorbent core 28 while still preventing exudates from passing through the backsheet 30 by, for example, being supplied with microapertures as described, for example, in U.S. Pat. No. 4,681,793. The backsheet may also be biodegradable such as the film disclosed in co-pending, commonly-assigned, U.S. patent application Ser. No. 07/721,066 "Disposable Absorbent Articles With Biodegradable Backsheets", Toms and Wnuk, filed on Jun. 26, 1991.

The size of the backsheet 30 is dictated by the size of the absorbent core 28 and the exact diaper design selected. In a preferred embodiment, the backsheet 30 has a modified hourglass shape extending beyond the absorbent core a minimum distance of at least about 1.3 cm to about 2.5 cm for baby diapers and 1.3 cm to about 6 cm for adult incontinent briefs around the entire diaper periphery 38.

The topsheet 26 of the body portion 22 of the present invention is compliant, soft feeling, and non-irritating to the wearer's skin. Further, the topsheet 26 is liquid pervious permitting liquids (e.g., urine) to readily penetrate through its thickness. A suitable topsheet 26 may be manufactured from a wide range of materials, such as porous foams, reticulated foams, apertured films; or woven or nonwoven webs of natural fibers (e.g. wood or cotton fibers), synthetic fibers (e.g., polyester or polypropylene fibers) or from a combination of natural and synthetic fibers. Preferably, it is made of a material that isolates the wearer's skin from liquids retained in the absorbent core 28.

There are a number of manufacturing techniques which may be used to manufacture the topsheet 26. For example, the topsheet 26 may be a non-woven web of fibers. When the topsheet comprises a nonwoven web, the web may be spunbonded, carded, wet-laid, meltblown, hydroentangled, hydroformed, combinations of the above, or the like. An exemplary topsheet 26 is carded and thermally bonded by means well known to those skilled in the fabric art and comprises staple length polypropylene fibers having a denier of about 2.2 and has a basis weight from about 15 to about 30 grams per square meter. As used herein, the term "staple length fibers" refer to those fibers having a length of at least about 15.9 mm (0.625 inches). This topsheet is manufactured by Veratec, Inc., a Division of International Paper Company, of Walpole, Mass. under the designation P-8. A particularly preferred topsheet for incontinent briefs of the present invention comprises a formed thermoplastic film such as that described in U.S. Pat. No. 3,929,135 entitled "Absorptive Structure Having Tapered Capillaries" which issued to Thompson on Dec. 30, 1975, and which patent is incorporated herein by reference.

The topsheet 26 and the backsheet 30 are joined together in any suitable manner as is well known in the diaper manufacturing art. As used herein, the term "joined" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members (e.g., absorbent core 28) which in turn are affixed to the backsheet 30. In a preferred embodiment, the topsheet 26 and the backsheet 30 are joined directly to each other in the diaper periphery 38 by a flap attachment means such as an adhesive or any other attachment means as is known in the art. In general, the core attachment means that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines, spirals, or spots of adhesive such as a network of adhesive filaments such as shown in U.S. Pat. No. 4,573,986, may be used.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. B2 3,860,003 entitled "Contractable Side Portions For a Disposable Diaper" issued to Buell on Jan. 14, 1975, describes a disposable diaper which provides a contractible leg opening having a side flap and elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. While each elasticized leg cuff 32 may be configured so as to be similar to any of the leg bands, side flaps, barrier cuffs, or elastic cuffs described above, it is preferred for the incontinent briefs of the present invention that each elasticized leg cuff 32 comprise a side flap 34 and one or more elastic members 36 such as shown in FIG. 1.

The diaper may also further comprise an elastic waist feature that provides improved fit and containment or any other features typically provided on diapers or incontinent garments as are known in the art. An exemplary elasticized waist feature is described in U.S. Pat. No. 4,515,595 issued to Kievet and Osterhage on May 7, 1985, and which is incorporated herein by reference.

The diaper 20 is provided with an adhesive fastening system 24 for forming a side closure on each side of the diaper 20. Thus, the diaper 20 is fitted to the wearer and the first end region 48 and the second end region 50 are maintained in an overlapping configuration when the diaper 20 is worn such that lateral tensions are maintained around the circumference of the diaper to maintain the diaper on the wearer.

In a preferred embodiment of the present invention as shown in FIG. 1, the fastening system 24 comprises two elements, a closure member 52 preferably comprising tape tabs 58 and a landing member 54, which are adhered to each other in use. The closure member 52 is intended to provide a means for engaging the landing member 54 so as to provide a secure bond or closure. Thus, the closure member 52 preferably comprises a fastening means for engaging the landing member. The closure member 52 also preferably comprises a means for positioning the fastening means adjacent the landing member so as to provide a bond. Preferred closure members comprise an inner fastening member or a tape tab.

An inner fastening member comprises a strip, patch, or layer of adhesive positioned on the body portion of the diaper. Exemplary examples of inner fastening members are described in U.S. Pat. No. 4,699,622 entitled "Disposable Diaper Having An Improved Side Closure" issued to Toussant and Hasse on Oct. 13, 1987; U.S. Pat. No. 5,019,072 issued to Polski on May 28, 1991; and U.S. Pat. No. 4,850,988, issued to Aledo et al. on Jul. 25, 1989, each of which are incorporated herein by reference.

As shown in FIG. 1, each closure member 52 preferably comprises a tape tab 58. At least one tape tab 58 is disposed adjacent each longitudinal edge 40 of the body portion 22 in the first end region 48 of the diaper 20. (For large incontinent briefs, two or more tape tabs are positioned on each longitudinal side such as is shown in the above-referenced U.S. Pat. No. 4,253,461; however, for simplicity purposes, FIG. 1 shows only one tape tab on each side.) Each tape tab 58 has a fixed end 61 and a connective end 62. The fixed end 61 (i.e., that end of the tape tab 58 joined to the body portion 22 during manufacture) is permanently attached to the body portion 22. The term "permanently attached", as used herein, refers to an attachment which does not release under normal usage conditions of a disposable diaper 20. The connective end 62 is that end of the tape tab 58 that extends outwardly from the body portion 22 beyond the longitudinal edge 40 and that is grasped by the diaperer in securing the diaper on the wearer. The connective end 62 has a fastening surface 60 onto which a layer of adhesive is coated. In a preferred embodiment of the fastening system 24 shown in FIG. 1, each tape tab 58 preferably further comprises a release tape 63 joined to the topsheet 26. The release tape 63 allows the connective end 62 to be inwardly folded during manufacture to protect the adhesive on the fastening surface 60 from contamination or delamination prior to use. An alternative configuration for the tape tab is a Y-bond construction such as is shown and explained in detail in U.S. Pat. No. 3,848,594 entitled "Tape Fastening System For Disposable Diapers" which issued to Kenneth B. Buell on Nov. 19, 1974, and which patent is incorporated herein by reference.

Optionally, the tape tab 58 can be provided with grip tabs at the distal edge of the tape tab 58. Grip tabs may be formed, for example, by folding part of the fastening surface 60 at the lateral outside end of the connective end 62 onto itself. Grip tabs are preferably 2 mm to 8 mm, more preferably about 3 ram, wide. Grip tabs can also be provided by having the distal edge not covered by adhesive. Additionally, the distal edge of the tape tab 58 may be provided with rounded corners for additional user comfort.

The tape tab 58 comprises a tape backing material which can be any of the tape backing materials well known in the art. For example, polyester films, polypropylene films, paper backings, or other materials which provide the required strength to be useful as part of a tape tab 58 during use of a diaper, are suitable for use as the tape backing material. Particularly, tape backing materials of polypropylene film having a caliper of about 0.15 mm have been found to perform satisfactorily. The same materials used for the tape backing material can be used for the release tape 63. In order to perform its release function, the side of the release tape that is not attached to the topsheet 26 can be coated with a release agent, preferably with a silicone release coating which is well known in the art.

The connective end 62 has a fastening surface 60 having a layer of adhesive coated onto the tape backing material. (As used herein, the term "coated" is not to be limited to any specific technique or method for applying the adhesive onto the tape backing material). The fastening system may use any suitable adhesive that provides the desired shear hang times, quick-stick, releasability from the landing member, and coat weight properties. The composition of the adhesive is not as important as the properties of the overall tape system as discussed hereinafter. The adhesive can, for example, be a hot melt adhesive which is coated onto the tape backing by any of the well known hot melt coating processes (e.g., by a slot coating process). Alternatively, the adhesive can be supplied in a solvent coating process. Preferably, the adhesive is an elastomeric pressure-sensitive adhesive. It is particularly preferred that such an adhesive material comprises a tackified rubber elastomer. As described hereinafter, the adhesive has preferable shear hang times, quick stick value, and releasability in conjunction with relatively low coating weights so as to provide the enhanced performance described herein. In accordance with the present invention, it has been found that tapes (tape backing material and adhesive) such as are manufactured by the Minnesota Mining and Manufacturing Company, St. Paul, Minn., under the designation KS 1294, have been found to provide satisfactory performance in the fastening system of the present invention.

The joining of the fixed end 61 to the body portion 22 can be provided by mechanical or preferably by adhesive means. In a preferred embodiment, the tape backing of the tape tab 58 is covered across its whole width with a layer of adhesive. This adhesive, thus, not only provides the fastening means at the connective end 62 but also the attachment to permanently adhere the tape tab 58 to the backsheet 30 at the fixed end 61.

The adhesive tape fastening system 24 further comprises a landing member 54. The landing member 54 provides a means for refastenably adhering itself and the adhesive disposed on the connective end 62 of the tape tab 58 together to form a secure but refastenable bond so as to provide a side closure for the diaper 20. The landing member 54 may be disposed anywhere on the outside surface 45 of the body portion 22 so long as it engages the tape tab 58. Typically, the landing member 54 is disposed in the second end region 50. The landing member 54 may either be a discrete separate element joined to the body portion 22 (e.g., a reinforcing member joined to the outer surface of the backsheet such as is shown in U.S. Pat. No. 4,710,190 issued to Wood et al. on Dec. 1, 1987 and incorporated herein by reference) or a unitary element that is neither divided nor discontinuous with an element of the diaper (e.g., only the backsheet 30 or a reinforcing member joined to the inner surface of the backsheet such that the adherence surface is the backsheet such as is disclosed in U.S. Pat. No. 3,867,940 issued to Mesek on Feb. 25, 1975 which is incorporated herein by reference). In a preferred embodiment of the present invention, the landing member comprises at least a portion of only the unreinforced backsheet 30. The adherence surface 31 of the landing member (generally the same surface as the outer surface of the backsheet 30) is the surface onto which the adhesive of the tape tab 58 is refastenably adhered during use of the diaper 20.

The properties of the overall fastening system, including the properties of the adhesive on the tape tabs and the properties of the landing member, are important design criteria in the performance of the adhesive fastening systems of the present invention on disposable absorbent articles. Fastening systems for disposable absorbent articles need to provide a bond at light application pressures that holds securely during wear and a bond under severe application pressures that can also be reopened and refastened without destruction or damage to the landing member. These values must be balanced against the environmental and economic need of reducing the materials and costs of such fastening systems. The shear hang times of the adhesive fastening system; the quick-stick property of the adhesive; the toughness of the backsheet; and the surface characteristics of the backsheet have been found to be important variables in providing not only superior bond security but also refastenability without the need for additional reinforcement of the landing member.

The shear hang time of the adhesive fastening system has been found to be a very reliable predictor of bond security in use. The object of the shear hang test is to measure how long an adhesive bond can hold against a given stress in the shear mode (i.e., shear hang time). Thus, the shear hang time evaluates the adhesive bond security, durability, under constant shear stress.

The standard shear hang test, as used in the present invention, is a test variation of PSTC No. 7. An adhesive surface of the tape tab having a width of 25.4 mm (1 inch) and a length of 25.4 mm (1 inch) is applied to the adherence surface of the landing member, the backsheet, which is reinforced on the side opposite the tape bond with an adhesive coated film whose properties are similar to the tape tab. Pressure exerted by a roller of 2043 grams (4.5 pounds) having a roll diameter of 100 mm (4 inches) and a width of 50 mm (2 inches) is applied to the tape tab. The test sample is conditioned at a temperature of about 37.8° C. (100° F.). A shear stress equivalent to an evenly distributed stress exerted by a 1000 gram weight is applied evenly across the width of the tape tab. The elapsed time until failure of the adhesive bond (i.e., releasing of the tape from the landing member) is measured. The shear hang time is generally related in a logarithmic way to other variables (area, stress, application pressure, temperature, in use performance, etc.). Thus, analysis of data and interpretation of data should be appropriate for logarithmic scales.

The preferred Standard Shear Hang Time, SHT, for adhesive fastening systems of the present invention for use on diapers should be greater than about 1000 minutes per square inch (log (SHT) of 3.0). However, for the adhesive fastening systems of the present invention, it has been found that Standard Shear Hang Times preferably greater than about 3000 minutes per square inch (log (SHT) of 3.5), more preferably greater than about 10,000 minutes per square inch (log (SHT) of 4.0) by optimizing the design criteria of the fastening system as described hereinafter. In fact, certain systems have been able to achieve Standard Shear Hang Times of greater than 15,000 minutes per square inch (log (SHT) of 4.2).

The art has typically used the standard shear hang test for qualifying adhesives for use on disposable absorbent articles (e.g., U.S. Pat. No. 4,655,761). However, the standard shear hang test is operated at very high temperatures and application pressures which are not indicative of the in-use conditions encountered by the adhesive fastening system such that the test does not assist in evaluating whether the properties of a particular adhesive are useful in the normal use of the fastening system. Thus, it has been found necessary, as a secondary test for bond security, to modify the standard shear hang test to be able to run the test under indicative conditions which simulate realistic in-use conditions.

The Modified Shear Hang Test used in the present invention evaluates the quality of the adhesive bond of the particular fastening system by using the specific unreinforced landing member (which simulates the low tensile strength of backsheets alone) and tape tab used in forming the adhesive fastening system of the diaper. An adhesive surface of the tape tab having a width of 25.4 mm (1 inch) and a length of 25.4 mm (1 inch) is applied to the adherence surface of the landing member, the backsheet, with a pressure exerted by a 250 g roller. (As a measuring tool for finished products where it is common that adhesive or other materials (such as the core) would interfere with the uniform application of pressure by a roller; an alternative method would be to place the sample on a balance and apply a measured 250 gram force by running the thumb across the sample.). The test sample is conditioned at a temperature of about 32.2° C. (90° F.). A shear stress equivalent to an evenly distributed stress exerted by a 750 g weight is applied evenly across the width of the tape tab. The elapsed time until failure of the adhesive bond (i.e., releasing of the tape from the landing member) is measured.

With these modifications to measure conditions that effect the tape failure rate, the Modified Shear Hang Test correlates with consumer measured tape failure rates across a wider range of adhesive/substrate designs versus the Standard Shear Hang Test. Lighter application pressures, use of the actual unreinforced landing member, and a realistic temperature range better simulates the user-made bond from which in-use failures occur. Thus, it is believed that the Modified Shear Hang Test of the present invention is a realistic test of how the adhesive bond behaves when it is under wearing tension on the diaper since it can simulate several failure mechanisms typically encountered by the adhesive fastening system (i.e., immediate failure due to inadequate surface adhesion and crack propagation or long term failure during the wearing period due to slow flow of adhesive under stress). The preferred Modified Shear Hang Time, MSHT, for adhesive fastening systems of the present invention for use on diapers should be greater than about 500 minutes per square inch (log (MSHT) of 2.7). However, for the adhesive fastening systems of the present invention, it has been found that Modified Shear Hang Times can be achieved of greater than about 1600 minutes per square inch (log (MSHT) of 3.1), more preferably greater than about 3000 minutes per square inch (log (MSHT) of 3.5) by optimizing the design criteria of the fastening system as described hereinafter.

The landing member 54, the backsheet 30, is preferably manufactured so as to provide an adherence surface 31 that will optimize the adherence, release, and refastenability of the tape tab 58. For both strong adhesion of the adhesive to the landing member and good bond security, the adherence surface of the landing member must be receptive to the adhesive at low application pressures. Typically, it has been found that a "smooth" adherence surface enhances bond security because the adhesive "wets" more of the surface. However, embossed adherence surfaces are generally considered more aesthetically pleasing for their matte appearance at a sacrifice to bond security since the entire area is not wetted by the adhesive. It has been discovered, however, that there is an optimum surface roughness for the adherence surface of the landing member, the backsheet, that increases the Shear Hang Time and Modified Shear Hang Time beyond what is achievable even with a "smooth" adherence surface.

The adherence surface 31 of the landing member 54, the backsheet 30, preferably has certain surface characteristics that are believed to enhance the bond security of the adhesive fastening system 24. Generally, the adherence surface does not exhibit a regular structure but contains a number of deviations which are divided into form, waviness and roughness. Of the various parameters of roughness, the Mean Leveling Depth, $R_{pm}$ [ISO/DIS 4287/IE or DIN 4768], is the parameter that most strongly correlates with bond security. The Mean Leveling Depth is the mean of five leveling depths of five successive sample lengths (1/5 of the evaluation length). The leveling depth is the largest of the depths as measured from the mean line (departures from the mean line). For a preferred embodiment of the present invention, the Mean Leveling Depth, $R_{pm}$, is between about 2 microns and about 20 microns, more preferably between about 2 microns and about 10 microns, and most preferably between about 3 microns and about 8 microns. The surface roughness (including the Mean Leveling Depth) is measured with a Perthometer S6P profilometer apparatus such as sold by Feinpruef of Blue Ash, Ohio. The Perthometer S6P is operated with a cut-off length of 2.5 mm (evaluation length of 12.5 mm) and a T9 FocoDyn laser probe which has better acuity and does not contact the surface as do diamond stylist probes.

According to the present invention, a landing member 54, preferably being a thermoplastic film, more preferably the backsheet 30, and having surface characteristics according to the above criteria, can have a texture, surface roughness, provided in a structured pattern or in a random pattern. In general, texturing of thermoplastic films is conducted by passing the film between a nip of a steel roll and a rubber roll. The steel roll contains the pattern such as, for example, square, round, random or other shapes as considered desirable for the particular usage of the thermoplastic film. The thermoplastic film is drawn into the nip between the two rolls which are pressed against each other. The depth of the texturing depends on the pattern provided on the steel roll. Depending on the thermoplastic film material, the steps of preheating of the thermoplastic film and cooling after the embossing can be added to the process. The adherence surface of the landing member has generally been that surface which is embossed by the steel roll. A more detailed description of texturing processes and apparatuses can be found in U.S. Pat. Nos. 4,436,520, 4,595,021, 4,546,029, 4,376,147 or WO 88/07336. However, according to the present invention, texturing of the thermoplastic film is provided by using a process in which, for example, a smooth non-patterned steel roll and a rubber roll are used in a similar way as described above. In this case, the surface of the material textured by the rubber roll is used as the adherence surface of the landing member. Preferably, the steel roll has a flat, sand blasted surface. The texturing of the adherence surface of the landing member results from the rubber roll.

As previously discussed herein, the toughness of the landing member, the backsheet, has been found to be an important variable in determining the refastenability of the adhesive fastening system. As used herein, the term "toughness" relates to the ability of a film to absorb a sudden impact of energy without the initiation of a crack or tear in the material. This parameter is important because one of the major failure mechanisms of tearing the landing member when the tape is removed for absorbent articles comes from the user jerking the tapes off of the product rather than peeling them off slowly. Thus, the landing member must be able to absorb this energy without failure. However, in the past, the focus on backsheet strength has been on the tensile properties only, with a resultant deficiency in toughness. Therefore, it has been found that enhanced refastenability of the fastening system is provided when the landing member has a toughness that exceeds a certain value as measured by the dropping dart impact test. In preferred embodiments of the present invention, the landing member, more particularly the backsheet, has been designed so as to have a toughness (as measured by the dropping dart impact test) of greater than about 1200 ergs of impact energy, more preferably greater than about 1600 ergs.

The toughness of the landing member as defined for the present invention is measured in accordance with ASTM Method D 1709-85 with certain modifications. (The ASTM Method D 1709-85 is incorporated herein by reference.) The modifications to the standard test method are as follows: 1) The diameter of the test area is 76 mm instead of 127 mm; 2) A fixed weight steel dart weighing 100 grams and having a smooth 19 mm diameter spherical surface on the leading edge is used instead of an adjustable weight dart; and 3) The impact energy (ergs) is adjusted by changing the drop height rather than the dart weight.

The landing member 54 is also selected so as to have a Youngs Modulus that more nearly correlates with the elasticity modulus of the tape tabs 58. The tape tabs typically have a very high Youngs Modulus of between about 175 N/mm$^2$ and about 310 N/mm$^2$. Thus, the landing member, more preferably the backsheet, is selected so as to have a Youngs Modulus of at least about 175 N/mm$^2$, more preferably greater than about 200 N/mm$^2$, most preferably greater than about 225 N/mm$^2$ so that the Young's Modulus of the landing member is increased to more nearly match that of the tape tabs. The Youngs Modulus is the elasticity modulus of a material (i.e., a material constant) describing the elastic behavior of the backsheet under stress. The higher the Youngs Modulus, the less elongation that results from a given force applied to the member. In other words, a landing member having a higher Youngs Modulus can withstand higher stress at the same elongation than a landing member having a lower Youngs Modulus. While not wishing to be bound by any particular theory, it is believed that by reducing the elongation of the landing member under stress by requiring a relatively high Youngs Modulus of greater than about 175 N/mm$^2$, a more stable adhesive interface between the adhesive and the landing member is provided. On the other hand, it is believed that if a landing member has a Youngs Modulus lower than about 175 N/mm$^2$, it will elongate relatively easily under stress thereby causing the adhesive interface between the tape tab and the backsheet to deform along with the elongation of the backsheet. This elongation must be compensated for by the adhesive of the tape tab along the adhesive surface. It is believed that the internal compensation of the adhesive would reduce the bond strength leading to debonding (i.e., failure of the adhesive fastening system).

The Youngs Modulus as defined for the present invention is measured in accordance with ASTM Method D 882-83 with certain modifications, that method is incorporated herein by reference. (Care should be taken to distinguish between the Youngs Modulus as defined in this test procedure versus other elasticity moduli which may have been used or measured previously and disclosed in the prior art.) The elasticity moduli previously disclosed, including patents referred to herein, are well below the required Youngs Modulus recognized by the present invention as being a lower threshold for providing the landing member of the fastening system.) In particular, the ASTM Method A of D882-83 "Constant Rate of Grip Separation Test" to measure the elasticity modulus as defined by the ASTM method is used with only minor alterations. In the following description, particular alterations used in measuring Youngs Modulus according to the present invention are indicated. A test sample for evaluating the Youngs Modulus is 25 mm in width and 200 mm in length. The length direction of the sample is parallel to the lateral direction of the absorbent article. Test samples are evaluated in their length direction and conditioned according to the ASTM method. The apparatus used in evaluating the Youngs Modulus can be any tensile testing machine commercially available having a constant rate of grip separation. An Instron 4201 machine such as distributed by the Instron Engineering Corporation, Canton, Mass. has been found to be particularly useful. Supply grips are also supplied from Instron in accordance with the ASTM method. The initial grip distance is fixed at 50.8 mm. The speed of testing is fixed at 508 mm/minute. Other provisions of the test procedure as well as calculation of the elastic modulus are done according to the ASTM method.

The quick-stick property of the adhesive is also important in providing for the initial bond strength and, to a lesser extent, refastenability of the fastening system. The quick-stick property of the adhesive measures the ability of the adhesive to wet the surface and form strong adhesive bonds at low application pressures. The quick-stick of the adhesive should be high enough to provide good bond security and high shear hang time, but not so high that it exceeds the toughness of the landing member to insure good refastenability. The quick-stick properties of the adhesive of the present invention is preferably greater than about 150 g/cm, more preferably greater than about 200 g/cm. The optimum of quick-stick for the entire fastening system of the present invention is greater than about 300 g/cm for secure fastening of the diaper. The quick-stick test is performed by placing a 25.4 mm width of the tape onto the landing member and removing the tape at a 90° angle. This test is thus a modification of PSTC No. 5 by using the landing member as the substrate and a 17.1 $g/cm^2$ application pressure.

The improved bond security and refastenability of the adhesive fastening system can be achieved without the need for reinforcing the landing member and with a minimum of materials. Preferred coating weights for the adhesives that provide an optimum balance between bond security and refastenability are different for each adhesive. Higher coat weights would typically provide stronger adhesive bonds at minimum application pressure while lower coat weights typically reduce the likelihood of tearing the landing member. It has been found, however, for the adhesive fastening systems of the present invention for use on disposable absorbent articles such as diapers, that the optimum coat weight of the preferred adhesive occurs preferably below about 22 $g/m^2$. More preferably, the optimum coat weight is between about 14 $g/m^2$ and about 18 $g/m^2$, most preferably between about 15 $g/m^2$ and about 16 $g/m^2$. The backsheet, which does not need to be reinforced, can also have a relatively low calculated caliper, to reduce material costs, of between about 0.025 mm (1 mil) and about 0.036 mm (1.4 mils).

The ability to remove the tape tab without tearing the landing member (i.e., refastenability) can be measured in the lab as well as in the consumers hands. In a lab test, the tape is put on as firmly as is possible and then the frequency that it tears the landing member upon being removed in a realistic way is measured. To put the tape on as firmly as possible, the tape is put on the landing member and warmed to 37.8° C. (100° F.) for 30 minutes or more. It is then rolled on with a 2.2 kg roller and left at 37.8° C. (100° F.) for another 30 minutes. After cooling to room temperature for at least 30 minutes, the tape tabs are removed by pulling rapidly as the typical consumer would. Any tearing of the landing member is considered a failure. This test provides the worst case and is about 6 times higher than the average landing member tearing experience in actual use. For the adhesive fastening systems of the present invention, the refastenability for the most severe lab test above is preferably greater than about 90%, more preferably greater than about 95%, and most preferably greater than about 98%.

While particular embodiments of the present invention have been illustrated and described, it would be obvious to those skilled in the art that various other changes and modifications can be made without departing from the spirit and scope of the present invention. It is therefore intended to cover in the appended claims all such changes and modifications that are within the scope of this invention.

What is claimed is:

1. A disposable absorbent article comprising:
    a body portion having a first end region, a second end region, longitudinal edges, and end edges, said body portion comprising a liquid pervious topsheet, a liquid impervious backsheet joined to said topsheet, and an absorbent core disposed between said topsheet and said backsheet; and
    an adhesive tape fastening system comprising:
    a) a tape tab disposed adjacent each longitudinal edge of said body portion in said first end region, each of said tape tabs having a fixed end and a connective end having a fastening surface, said fixed end being joined to said body portion, said connective end extending laterally outward from said longitudinal edge of said body portion, and said fastening surface being coated with an adhesive; and
    b) a landing member for refastenably adhering to said adhesive to form a bond during use of the absorbent article, said landing member having an adherence surface which consists of a portion of said backsheet in said second end region, said backsheet having an average nominal caliper of between about 0.020 mm and about 0.036 mm, said adherence surface having a surface roughness defined by a Mean Leveling Depth of between about 2 microns and about 10 microns, and
    wherein said tape fastening system has a Standard Shear Hang Time of greater than about 3000 minutes per square inch and a Modified Shear Hang Time of greater than about 750 minutes per square inch.

2. The absorbent article of claim 1 wherein said backsheet has a Young's Modulus of greater than about 175 $N/mm^2$.

3. The absorbent article of claim 2 wherein said backsheet has a toughness of greater than about 1200 ergs.

4. The absorbent article of claim 3 wherein said adhesive has a quick stick of greater than about 150 g/cm.

5. The absorbent article of claim 1 wherein said backsheet has a toughness of greater than about 1200 ergs.

6. The absorbent article of claim 5 wherein said adhesive has a quick stick of greater than about 150 g/cm.

7. The absorbent article of claim 1 wherein said adhesive has a coat weight of less than about 22 g/m$^2$.

8. The absorbent article of claim 1 wherein said backsheet has an average nominal caliper of between about 0.025 mm and about 0.030 mm.

9. A disposable absorbent article comprising:
a body portion having a first end region, a second end region, longitudinal edges, and end edges, said body portion comprising a liquid pervious topsheet, a liquid impervious backsheet joined to said topsheet, and an absorbent core disposed between said topsheet and said backsheet; and
an adhesive tape fastening system comprising:
a) a tape tab disposed adjacent each longitudinal edge of said body portion in said first end region, each of said tape tabs having a fixed end and a connective end having a fastening surface, said fixed end being joined to said body portion, said connective end extending laterally outward from said longitudinal edge of said body portion, and said fastening surface being coated with an adhesive, wherein the coat weight of said adhesive is between about 14 g/m$^2$ and about 18 g/m$^2$; and
b) a landing member for refastenably adhering to said adhesive to form a bond during use of the absorbent article, said landing member having an adherence surface which consists of a portion of said backsheet in said second end region, said backsheet having an average nominal caliper of between about 0.020 mm and about 0.036 mm, said backsheet having a Youngs Modulus of greater than about 200 N/mm$^2$, and a toughness of greater than about 1600 ergs, the adherence surface having a surface roughness defined by a Mean Leveling Depth of between about 3 microns and about 8 microns; and
wherein said adhesive has a quick stick value of less than about 200 g/cm, and wherein said fastening system has a Standard Shear Hang Time of greater than about 3000 minutes per square inch and a Modified Shear Hang Time of greater than about 750 minutes per square inch.

10. The absorbent article of claim 9 wherein fastening system has a Modified Shear Hang Time of greater than about 1000 minutes/square inch.

11. The absorbent article of claim 9 wherein the absorbent article is an adult incontinent brief.

12. The absorbent article of claim 9 wherein the absorbent article is a baby diaper.

* * * * *

UNITED STATES PATENT AND TRADEMARK OFFICE
CERTIFICATE OF CORRECTION

PATENT NO. : 5,399,177
DATED : March 21, 1995
INVENTOR(S) : Ted L. Blaney et al.

It is certified that error appears in the above-indentified patent and that said Letters Patent is hereby corrected as shown below:

Column 5, line 38    delete "rail" and insert --mil--.
Column 6, line 27    delete "previous" and insert --pervious--.
Column 7, line 17    delete "conform" and insert --coform--.
Column 11, line 42   delete "ram" and insert --mm--.

Signed and Sealed this

Eighth Day of July, 1997

Attest:

BRUCE LEHMAN

*Attesting Officer*   *Commissioner of Patents and Trademarks*